(12) United States Patent
Johnson et al.

(10) Patent No.: US 7,355,066 B1
(45) Date of Patent: Apr. 8, 2008

(54) PROCESS FOR MAKING TERPENE ESTERS

(75) Inventors: Walter E. Johnson, Jacksonville, FL (US); C. Rodney Gorman, Orange Park, FL (US)

(73) Assignee: Millenium Specialty Chemicals, Inc., Houston, TX (US)

( * ) Notice: Subject to any disclaimer, the term of this patent is extended or adjusted under 35 U.S.C. 154(b) by 0 days.

(21) Appl. No.: 11/633,275

(22) Filed: Dec. 4, 2006

(51) Int. Cl.
*C07C 67/00* (2006.01)
*C07C 67/48* (2006.01)

(52) U.S. Cl. ............. 560/239; 560/248; 560/249

(58) Field of Classification Search ............... None
See application file for complete search history.

(56) References Cited

U.S. PATENT DOCUMENTS

| | | | | |
|---|---|---|---|---|
| 4,008,256 | A | | 2/1977 | Renvall et al. ............ 260/347.4 |
| 4,571,426 | A | * | 2/1986 | Gude et al. ................. 549/257 |
| 7,064,102 | B2 | | 6/2006 | Eh ............................... 512/22 |

OTHER PUBLICATIONS

Saravanan, et al., *Tetrahedron Letters 40* (1999) 2611.
Orita, et al., *J. Org. Chem. 66* (2001) 8926.
Chakraborti, et al., *Synthesis* (2004) 111.
Menger, et al., *J. Org. Chem. 50* (1985) 3928.
Wei, et al., *J. Appl. Polym. Sci. 84* (2002) 1087.
Hö fle, et al., *Angew. Chem. I.E.* (1978) 569 at p. 573.
Höfle, et al., *Synthesis* (1972) 619.

* cited by examiner

*Primary Examiner*—Yvonne Eyler
*Assistant Examiner*—Yevgeny Valenrod
(74) *Attorney, Agent, or Firm*—Jonathan L. Schuchardt

(57) ABSTRACT

A process for making terpene esters is disclosed. Reaction of a terpene alcohol with acetic anhydride in the presence of a high-boiling amine provides a terpene ester. Acetic acid, which is distilled from the reaction mixture as it forms can be recovered. The terpene ester is distilled from the high-boiling amine to provide a product that is substantially free of nitrogen-containing impurities. The reaction mixture can be reused for subsequent acylations. The simple, economical process gives high-quality terpene esters while avoiding waste-disposal issues of other common acylation procedures.

12 Claims, No Drawings

PROCESS FOR MAKING TERPENE ESTERS

FIELD OF THE INVENTION

The invention relates to a process for making terpene esters, particularly acetate esters. The esters are valuable ingredients of flavors and fragrances.

BACKGROUND OF THE INVENTION

Terpene alcohols and esters occur naturally in many essential oils. The oils, or their components, are ubiquitous in flavor and fragrance applications. Synthetic routes to the more important terpene esters, such as linalyl acetate, geranyl acetate, and citronellyl acetate, have been developed and commercialized. Linalyl acetate occurs naturally in lavender (>50%), bergamot (27%), petitgrain bigarade (44%), clary sage (45-60%), and neroli (6%) oils. Geranyl acetate is found in coriander (16%), palmarosa (8-17%), and citronella (5-8%) oils, among others. Terpinyl acetate is a major component (24%) of cardamom oil. Other naturally occurring terpene esters include citronellyl, lavandulyl, bornyl, and neryl acetates.

As with other alcohols, terpene alcohols are conveniently converted to the corresponding acetate esters by reacting them with acetic anhydride. The reaction is normally performed in the presence of a catalyst. Reported catalysts are common, such as p-toluenesulfonic acid or sodium acetate, or more esoteric, such as copper(II) triflate (*Tetrahedron Lett.* 40 (1999) 2611), bismuth(III) triflate (*J. Org. Chem.* 66 (2001) 8926), copper(II) tetrafluoroborate (*Synthesis* (2004) 111), and polymer-bound amines (*J. Org. Chem.* 50 (1985) 3928; *J. Appl. Polym. Sci.* 84 (2002) 1067).

More commonly, however, the acylation is performed in the presence of a stoichiometric amount of a low-boiling amine such as pyridine or triethylamine (see U.S. Pat. No. 4,008,256 and *Angew. Chem. I.E.* (1978) 569), which accelerates the acylation and neutralizes the acetic acid by-product. A catalytic amount of 4-(dimethylamino)pyridine or 4-(1-pyrrolidino)pyridine can be used to further speed the reaction, particularly for difficult acylations such as ones that involve tertiary terpene alcohols. The pyridinium acetate or triethylammonium acetate salt is eliminated by water washing using a typical organic workup. Such common workups are illustrated by the preparation of linalyl acetate from linalool (*Synthesis* (1972) 619 and *Angew. Chem. I.E.* (1978) 569 at page 573) and, more recently, by the preparation of 1-cyclohexyl-1-methylethyl acetate from 2-cyclohexyl-2-propanol (U.S. Pat. No. 7,064,102).

Unfortunately, it is often impractical, especially in an industrial context, to generate a waste stream that contains pyridinium or trialkylammonium acetate salts. Ideally, the acetic acid generated during acylation would be recovered. Thus, a preferred process would acylate terpene alcohols without using a molar equivalent of pyridine or triethylamine, and without generating a waste stream.

In the typical acylation process with acetic anhydride and a low-boiling amine, the amine helps to avoid acid-catalyzed side reactions (such as dehydration or isomerization) by neutralizing acetic acid as it forms. Such side reactions are particularly important when the terpene alcohol is tertiary and/or unsaturated (as with linalool). Consequently, simply eliminating the low-boiling amine is not a workable solution; the side reactions still need to be avoided.

Moreover, fragrance-quality terpene esters must be substantially free of nitrogen-containing impurities. Thus, it is unacceptable to use an excess of pyridine or triethylamine because traces of these amines, if used for acylation, will usually be present in even a carefully distilled terpene ester.

The flavor and fragrance industry would benefit from an improved way to make and purify terpene esters. In particular, a way to acylate terpene alcohols while recovering acetic acid and avoiding aqueous waste streams is needed. A valuable process would be simple to practice without an esoteric catalyst and would afford fragrance-quality terpene esters. The ability to recover and reuse the catalyst is also desirable. Ideally, the process could be used to make a variety of terpene esters known to be valuable flavor or fragrance components.

SUMMARY OF THE INVENTION

The invention is a process for making terpene esters. In the process, a terpene alcohol reacts with acetic anhydride in the presence of a high-boiling amine to produce a reaction mixture comprising a terpene ester. Acetic acid is distilled from the reaction mixture as it forms. The terpene ester is then distilled from the high-boiling amine to provide a purified product that is substantially free of nitrogen-containing impurities.

We surprisingly found that by including a high-boiling amine in the reaction mixture, high-quality terpene esters can be obtained while avoiding the waste-stream issues of other common acylation procedures, particularly ones that use a low-boiling amine and an extractive workup. Distillation of acetic acid from the reaction mixture as it forms permits recovery of this by-product. Moreover, after the terpene ester is recovered by distillation, the reaction mixture can be reused for subsequent acylation reactions with fresh terpene alcohol and acetic anhydride. In sum, the invention provides a simple, economical way to make flavor or fragrance-quality terpene esters.

DETAILED DESCRIPTION OF THE INVENTION

The process of the invention reacts a terpene alcohol with acetic anhydride in the presence of a high-boiling amine. Any desired grade of acetic anhydride can be used. Reagent (98+%) or technical (95+%) grade materials are desirable, but cruder grades can be tolerated. The acetic anhydride can be recovered material from an earlier acylation run, and it can contain a substantial proportion of acetic acid.

The anhydride reacts with a terpene alcohol. Terpene alcohols are a well-defined class of compounds that are based on five-carbon isoprene units and have at least one hydroxyl group, which can be primary, secondary, or tertiary. Most terpene alcohols have ten, fifteen, or twenty carbons. The terpene alcohols can be acyclic or cyclic, and saturated or unsaturated, but all are branched. Preferred terpene alcohols are those having value for the flavor and fragrance industry when converted into an acetate ester. Tertiary, unsaturated alcohols are particularly preferred. Suitable terpene alcohols include, for example, linalool, geraniol, citronellol, nerol, α-terpineol, borneol, terpinen-4-ol, limonen-4-ol, carveol, lavandulol, menthol, 8-p-cymenol, pinanol, dihydromyrcenol, myrcenol, and the like, and mixtures thereof. Linalool is particularly preferred.

The relative amounts of acetic anhydride and terpene alcohol used will depend on several factors, including the desired reaction and conversion rates, temperature, the nature of the terpene alcohol, and other considerations. Generally, however, it is desirable to use at least a slight excess of acetic anhydride. In particular, the amount of acetic anhydride used is preferably from 1.05 to 5, more preferably from 1.1 to 2, and most preferably from 1.2 to 1.6 moles per mole of terpene alcohol. Unreacted anhydride is conveniently recovered by distillation and reused in the acylation process.

The process is perfomed in the presence of a high-boiling amine. The high-boiling amine has a boiling point at least 20° C. greater than the boiling point of the terpene ester product. Suitable high-boiling amines preferably have a boiling point greater than about 300° C. at atmospheric pressure, or greater than about 150° C. at 0.7 mm Hg. More preferred high-boiling amines have a boiling point greater than about 160° C. at 0.7 mm Hg. Preferred high-boiling amines are $C_{18}$-$C_{40}$ aliphatic or cycloaliphatic amines, particularly tertiary amines. Particular examples include tri-n-hexylamine, tri-n-octylamine, tri-n-decylamine, tri-n-dodecylamine, tris(2-ethylhexyl)amine, N-ethyl-di-n-octylamine, N,N-dicyclo-hexyl-n-octylamine, di-n-decylmethylamine, di-n-dodecylmethylamine, and the like, and mixtures thereof. Tri-n-octylamine is particularly preferred.

The high-boiling amine is believed to play a number of key roles in the process of the invention. As a solvent, it helps to maintain a free-flowing liquid reaction mixture. Because it is high-boiling, the amine stays in the reaction mixture and helps to keep it liquified even after the reactants, acetic acid, and the terpene ester are distilled away. The high-boiling amine also buffers the reaction mixture. Use of the amine permits isolation of a flavor or fragrance-quality terpene ester, one that is substantially free of nitrogen-containing impurities. In contrast, the low-boiling amines normally used in acylations with acetic anhydride, if used in the instant process, will contaminate the terpene ester and render it, without further processing, unsuitable for most flavor or fragrance applications. Moreover, the high-boiling amine can be reused without the need to purify it for subsequent acylation runs.

The acylation reaction is preferably performed at a temperature within the range of 30° C. to 180° C., more preferably from about 60° C. to about 150° C.

The acylation reaction is usually reasonably complete within a few hours to a few days. The actual time needed depends on many factors, including temperature, the relative amounts of terpene alcohol and acetic anhydride, the nature of the alcohol, and other factors.

Optionally, a catalyst is included in the process to accelerate the acylation reaction. Preferred catalysts are pyridine derivatives such as dialkyl-aminopyridines, pyrrolidinopyridines, or piperidinopyridines. Examples include 4-(dimethylamino)pyridine (DMAP), 4-(1-pyrrolidino)pyridine, or 4-(1-piperidino)-pyridine. The amount of acylation catalyst used is preferably in the range of about 0.001 to about 1 moles of catalyst per mole of terpene alcohol.

The reactants can be combined in any desired order. In one approach, the terpene alcohol is added to a heated mixture of acetic anhydride and the high-boiling amine. It is also acceptable to add the acetic anhydride to a mixture of the terpene alcohol and the high-boiling amine. In still another approach, the terpene alcohol and the acetic anhydride are added simultaneously to the high-boiling amine.

Acetic acid is distilled from the reaction mixture as it forms in the acylation process. The distillation is preferably performed at or below atmospheric pressure. Preferably, the acetic acid is removed with the assistance of a partial vacuum, preferably from about 20 mm to about 400 mm Hg, and more preferably from about 100 mm to about 250 mm Hg. Removing the acetic acid allows for its recovery and possible reuse. If desired, for example, the acetic acid can be dehydrated to produce more acetic anhydride. Distillation of acetic acid also obviates the need to remove and dispose of a large amount of an acetate salt with an extractive workup as is typically needed when a low-boiling amine is used. Usually, some unreacted acetic anhydride codistills with the acetic acid.

After the the acetic acid is removed, the terpene ester is distilled from the reaction mixture. This distillation is performed at or below atmospheric pressure, preferably under vacuuum. The terpene ester is normally distilled at a pressure in the range of about 0.1 to about 50 mm Hg, more preferably from about 0.1 to about 10 mm Hg. The high-boiling amine remains in the distillation pot, so the terpene ester is obtained substantially free of nitrogen-containing impurities. "Substantially free" means that the amount of nitrogen-containing compounds in the distilled terpene ester is less than 1 ppm, and preferably is not detectable, by gas chromatography analysis.

A wide variety of terpene esters can be made using the process of the invention. Examples include linalyl acetate, geranyl acetate, citronellyl acetate, neryl acetate, α-terpinyl acetate, bornyl acetate, terpinenyl acetate, limonenyl acetate, carvyl acetate, lavandulyl acetate, menthyl acetate, 8-p-cymenyl acetate, pinanyl acetate, dihydromyrcenyl acetate, myrcenyl acetate, and the like, and mixtures thereof. Linalool is particularly preferred.

The distillation residue is advantageously reused for subsequent acylation reactions. Thus, the distillation residue that contains the high-boiling amine can be reused with fresh terpene alcohol and acetic anhydride to produce more terpene ester. As illustrated in the preparation of linalyl acetate, Examples 1 and 2 below show that the residue can be reused multiple times while maintaining high yields of the desired acetate.

In a preferred process of the invention, illustrated by Examples 1 and 2, linalool is converted to linalyl acetate. Linalool reacts with acetic anhydride in the presence of a high-boiling amine (e.g., tri-n-octylamine) at a temperature in the range of 60° C. to 180° C. to produce linalyl acetate. Acetic acid is distilled from the reaction mixture as it forms at or below atmospheric pressure. The terpene ester product is vacuum distilled from the high-boiling amine to obtain linalyl acetate that is substantially free of nitrogen-containing impurities.

The following examples merely illustrate the invention. Those skilled in the art will recognize many variations that are within the spirit of the invention and scope of the claims.

EXAMPLE 1

Preparation of Linalyl Acetate Using Tri-n-octylamine and DMAP

A reaction flask equipped with a reflux column, condenser, addition funnel, take-off adapter, and magnetic stirrer is charged with acetic anhydride (1000 g, 9.80 mol), 4-(dimethylamino)pyridine ("DMAP," 15 g), and tri-n-octylamine (100 g). The mixture is stirred and heated using an external oil bath to a pot temperature of 125° C. Linalool (1000 g, 94.6% pure, 6.14 mol) is added dropwise over about 1-2 hours while maintaining reflux. As the reaction proceeds, acetic acid is continuously removed overhead by distillation at 200 mm Hg. The reaction is deemed to be reasonably complete after 12-14 hours. Residual acetic acid and unreacted acetic anhydride are removed by distillation at 200 mm Hg. Continued distillation at 2 mm Hg provides an initial cut (546 g) that contains, by gas chromatography (GC) analysis, linalyl acetate (85.5%) and linalool (2.2%) along with acetic anhydride (5.3%) and acetic acid (0.5%). A later fraction contains 657 g of 96% pure material. Total linalyl acetate obtained from Run 1: 1099 g (91% from linalool).

The distillation residue is used to prepare more linalyl acetate from fresh acetic anhydride (1000 g) and linalool (1000 g of 94.6% pure material) in the manner described above. The reaction mixture is heated to reflux before starting the linalool addition. The initial distillation fraction (512 g) contains 477 g (93%) of linalyl acetate. A later fraction contains 720 g of 96% pure material. Total linalyl acetate obtained from Run 2: 1166 g (97%).

The distillation residue is used for a third, identical preparation. The initial fraction (521 g) contains 482 g (92%) of linalyl acetate. A later fraction contains 696 g of 96% pure material. Total linalyl acetate obtained from Run 3: 1149 g (95%).

Three-run total for linalyl acetate: 3414 g (95%).

EXAMPLE 2

Preparation of Linalyl Acetate using only Tri-n-octylamine

To test the recyclability of the high-boiling amine, a series of six consecutive runs is performed with the same tri-n-octylamine.

The procedure of Example 1 is generally followed with linalool (1000 g of 94.6% pure material), acetic anhydride (1000 g), and tri-n-octylamine (100 g), except that DMAP is not included. The reaction is deemed to be reasonably complete after 20-28 hours. The initial distillation fraction (569 g) contains 397 g (70%) of linalyl acetate. A later fraction contains 724 g of 93% pure material. Total linalyl acetate obtained from Run 1: 1074 g (89%).

The distillation residue is used for a second run with 1190 g of acetic anhydride. The initial fraction (515 g) contains 380 g (74%) of linalyl acetate. A later fraction contains 783 g of 93% pure material. Total linalyl acetate obtained from Run 2: 1109 g (92%).

The distillation residue is used for a third run with 1400 g of acetic anhydride. The initial fraction (565 g) contains 381 g (68%) of linalyl acetate. A later fraction contains 808 g of 91% pure material. Total linalyl acetate obtained from Run 3: 1117 g (93%).

Three more identical runs are performed using 1400 g of acetic anhydride for each run. Total linalyl acetate obtained from Runs 4-6: 3090 g (86%). The final pot residue contains, in addition to the tri-n-octylamine and unidentified nonvolatile materials, about 90 g of neryl and geranyl acetates.

Six-run total for linalyl acetate: 6390 g (89%)

EXAMPLE 3

Preparation of Geranyl Acetate

A reaction flask equipped as in Example 1 is charged with acetic anhydride (600 g, 5.9 mol), DMAP (7.5 g), and tri-n-octylamine (50 g). The mixture is heated to reflux (about 125° C.), and geraniol/nerol mixture (500 g) is added dropwise over about 1 hour. Acetic acid is continuously removed overhead by distillation (200 mm Hg). When GC analysis shows that conversion is complete, residual acetic acid and unreacted acetic anhydride are removed by distillation at 200 mm Hg. Continued distillation at 2 mm Hg provides crude geranyl acetates (640 g, 92% yield) having a purity of about 91%.

EXAMPLE 4

Preparation of α-Terpinyl Acetate

The procedure of Example 3 is generally followed using α-terpineol (500 g) instead of geraniol. Distillation provides crude α-terpinyl acetate (655 g, 93% yield) having a purity of about 90%.

EXAMPLE 5

Preparation of Limonen-4-yl Acetate

The procedure of Example 3 is generally followed using limonen-4-ol (500 g) instead of geraniol. Distillation provides crude limonen-4-yl acetate (660 g, 91% yield) having a purity of about 87%.

EXAMPLE 6

Preparation of Carvyl Acetate

The procedure of Example 3 is generally followed using a mixture of carveol isomers and carvone (500 g) instead of geraniol. Distillation provides a crude mixture of carvone and carvyl acetates (625 g, 86% yield) having a purity of about 74%.

The examples are meant only as illustrations. The following claims define the invention.

We claim:

1. A process which comprises reacting a terpene alcohol with acetic anhydride in the presence of a $C_{18}$-$C_{40}$ aliphatic tertiary high-boiling amine to produce a reaction mixture comprising a terpene ester, distilling acetic acid from the reaction mixture as it forms, and isolating a purified terpene ester from the high-boiling amine by distillation, wherein the purified terpene ester is substantially free of nitrogen-containing impurities.

2. The process of claim 1 wherein the terpene alcohol is selected from the group consisting of linalool, geraniol, citronellol, nerol, α-terpineol, borneol, terpinen-4-ol, limonen-4-ol, carveol, lavandulol, menthol, 8-p-cymenol, pinanol, dihydromyrcenol, myrcenol, and mixtures thereof.

3. The process of claim 1 wherein the terpene alcohol is a tertiary, unsaturated terpene alcohol.

4. The process of claim 1 wherein the terpene alcohol is linalool.

5. The process of claim 1 wherein the high-boiling amine is tri-n-octylamine.

6. The process of claim 1 wherein the reaction is performed at a temperature within the range of 30° C. to 180° C.

7. The process of claim 1 wherein the reaction is performed in the presence of a dialkylaminopyridine catalyst.

8. The process of claim 1 wherein a distillation residue that contains the high-boiling amine is reused with fresh terpene alcohol and acetic anhydride to produce more terpene ester.

9. A process which comprises reacting linalool with acetic anhydride in the presence of a $C_{18}$-$C_{40}$ aliphatic tertiary high-boiling amine at a temperature in the range of 60° C. to 180° C. to produce a reaction mixture comprising linalyl acetate, distilling acetic acid from the reaction mixture as it forms at or below atmospheric pressure, and isolating purified linalyl acetate from the high-boiling amine by vacuum distillation, wherein the resulting purified linalyl acetate is substantially free of nitrogen-containing impurities.

10. The process of claim 9 wherein the reaction is performed in the presence of 4-(dimethylamino)pyridine.

11. The process of claim 9 wherein the linalool is added to a heated mixture of acetic anhydride and the high-boiling amine.

12. The process of claim 9 wherein the high-boiling amine is tri-n-octylamine.

* * * * *